United States Patent [19]
Samson

[11] Patent Number: 5,683,410
[45] Date of Patent: *Nov. 4, 1997

[54] SINGLE-LUMEN BALLOON CATHETER HAVING A DIRECTIONAL VALVE

[75] Inventor: Gene Samson, Milpitas, Calif.

[73] Assignee: Target Therapeutics, Inc., Fremont, Calif.

[*] Notice: The term of this patent shall not extend beyond the expiration date of Pat. No. 5,304,198.

[21] Appl. No.: 428,061

[22] PCT Filed: Nov. 4, 1993

[86] PCT No.: PCT/US93/10638

§ 371 Date: Apr. 27, 1995

§ 102(e) Date: Apr. 27, 1995

[87] PCT Pub. No.: WO94/11047

PCT Pub. Date: May 26, 1994

[51] Int. Cl.$^6$ .................................................. A61M 29/00
[52] U.S. Cl. ........................... 606/194; 604/96; 604/249; 128/772
[58] Field of Search ....................... 606/192, 194; 604/33, 96, 99, 101, 102, 103, 246, 249, 170; 128/772

[56] References Cited

U.S. PATENT DOCUMENTS

| | | |
|---|---|---|
| 396,754 | 1/1889 | Mayfield . |
| 1,878,671 | 9/1932 | Cantor . |
| 1,920,006 | 7/1933 | Dozier . |
| 3,467,101 | 9/1969 | Fogarty et al. . |
| 3,726,283 | 4/1973 | Dye et al. . |
| 3,795,246 | 3/1974 | Sturgeon . |
| 3,841,308 | 10/1974 | Tate . |
| 4,413,989 | 11/1983 | Schjeldahl et al. . |
| 4,606,347 | 8/1986 | Fogarty et al. . |
| 4,646,742 | 3/1987 | Packard et al. . |
| 4,848,344 | 7/1989 | Sos et al. . |
| 4,944,740 | 7/1990 | Buchbinder et al. . |
| 4,994,032 | 2/1991 | Sugiyama et al. . |
| 5,059,176 | 10/1991 | Winters . |
| 5,085,636 | 2/1992 | Burns . |
| 5,100,381 | 3/1992 | Burns . |
| 5,135,494 | 8/1992 | Engelson et al. . |
| 5,171,221 | 12/1992 | Samson . |
| 5,207,229 | 5/1993 | Winters . |

*Primary Examiner*—Michael Powell Buiz
*Assistant Examiner*—Cris L. Rodriguez
*Attorney, Agent, or Firm*—Morrison & Foerster

[57] ABSTRACT

This invention is a single-lumen balloon catheter having a valve seat on the distal end of the catheter, distal of the balloon, which may be operated by a control wire having a valve plug disposed on the wire. The valve seat may be engaged by the valve plug from either direction, depending on the installation of the control wire. In either event, if the valve plug is installed distally of the valve seat in the catheter lumen, the valve is closed by pulling on the control wire (or moving the control wire in a proximal direction) and introducing fluid through the catheter lumen through the balloon. Alternatively, the guidewire, with its integral valve plug, may be introduced from the proximal end of the catheter and may traverse the body of the balloon to engage the valve seat in the distal end of the catheter. Pushing on the control wire will seat the valve, allowing the introduction of fluid through the catheter lumen to inflate the balloon. The latter arrangement allows the control wire to be interchanged with other guidewires a physician may wish to use. The balloon provided for in this invention is of a single length and does not change its axial length as it is inflated.

11 Claims, 2 Drawing Sheets

SINGLE-LUMEN BALLOON CATHETER HAVING A DIRECTIONAL VALVE

FIELD OF THE INVENTION

This invention is a single-lumen balloon catheter having a valve seat on the distal end of the catheter, distal of the balloon, which may be operated by a control wire having a valve plug disposed on the wire. The valve seat may be engaged by the valve plug from either direction, depending on the installation of the control wire. In either event, if the valve plug is installed distally of the valve seat in the catheter lumen, the valve is closed by pulling on the control wire (or moving the control wire in a proximal direction) and introducing fluid through the catheter lumen through the balloon. Alternatively, the guidewire, with its integral valve plug, may be introduced from the proximal end of the catheter and may traverse the body of the balloon to engage the valve seat in the distal end of the catheter. Pushing on the control wire will seat the valve, allowing the introduction of fluid through the catheter lumen to inflate the balloon. The latter arrangement allows the control wire to be interchanged with other guidewires a physician may wish to use. The balloon provided for in this invention is of a single length and does not change its axial length as it is inflated.

BACKGROUND OF THE INVENTION

Angioplasty is an excellent method for treating a wide variety of vascular diseases. In particular, it has been used extensively for opening stenoses in coronary arteries. The process has been increasingly used for treatment of stenosis in other parts of the vascular system.

One of the more well known and widely practiced forms of angioplasty makes use of a dilatation catheter which has an inflatable balloon at is distal end. Using fluoroscopy, the physician guides the catheter through the vascular system until the balloon is properly positioned. By applying a fluid through the separate inflation lumen, the balloon is inflated. The balloon's inflation causes the artery to stretch and presses the lesion or stenose into the artery wall, thereby re-establishing after deflation of the balloon, increased blood flow through the artery.

In order to treat very tight stenoses, i.e., those having small openings, increasingly small catheter diameters are desirable. Significantly more flexible catheters are also desired in that otherwise very tight areas of stenosis will not be approachable. Although flexible and narrow of diameter, a good catheter must also be easily introduced and easily advanced through the tortuous path of the vascular system.

There are a variety of dilatation catheter types. Many use multiple lumens. For instance, a catheter may use a separate guidewire lumen so that a guidewire can be used to establish the path to the stenosis. The catheter may then be fed over the guidewire until the balloon is positioned over the stenosis. The catheter obviously has a separate lumen to allow introduction of and removal of fluid for the balloon.

Other catheter designs include those which act as their own guidewire, thereby eliminating the need for a separate guidewire lumen. Elimination of the need for the separate lumen means that the profile of the catheter can be somewhat smaller. Typical of such integral designs are U.S. Pat. No. 4,606,247, to Fogarty et al., which shows a catheter having an evertible balloon at is distal tip. The distal tip of the catheter is placed near the stenosis to be treated. The balloon is extended beyond the distal tip to a position within the stenosis and then inflated to press the lesion back into the wall of the vessel. The balloon contains a passageway in the middle having a plug of some elastomeric material through which a guidewire may be placed. The plug retains the pressure of the fluid on the balloon, whether the guidewire is present or not.

Another "over-the-wire" catheter is shown in U.S. Pat. No. 5,085,636, to Burns. The Burns device utilizes a balloon having a port for introducing fluid into the balloon and simultaneous device for not allowing fluid to pass through the catheter when a guidewire is present in the vicinity of the balloon. The fluid seal is distendible and does not allow fluid past the guidewire.

My U.S. patent application Ser. No. 07/650,808, filed Feb. 5, 1991 now U.S. Pat. No. 5,171,221 entitled "Single Lumen Low Profile Valved Balloon Catheter" discloses a single lumen balloon catheter having a catheter using a flexible guidewire which extends axially through the lumen beyond the open end of an intermediate balloon segment. The guidewire is axially movable within the lumen and has two discrete portions of different diameters. The first diameter, distal on the guidewire, is smaller that a second more proximal diameter on the guidewire. The larger guidewire meshes with the diameter of the lumen just proximal of the balloon thereby sealing it on the proximal end. Simultaneously at the distal end of the balloon a valve member mounted on the guidewire blocks the distal opening of the catheter.

None of the prior art shows a device in which a control wire having a valve plug mounted thereon, which meshes with a valve seat mounted within the lumen and in which the balloon maintains a constant axial length during its distension.

SUMMARY OF THE INVENTION

This invention is a single lumen valved balloon catheter assembly with a single lumen having a proximal end, an open distal end, a valve seat section located towards the distal end of the catheter having both distal and proximal valve surfaces. The catheter body has a balloon section proximal of the valve section having an inflatable balloon. The balloon segment or section includes therein a balloon inner member, the interior of which is generally colinear with the lumen in the catheter body, and which balloon inner member allows fluid communication between the catheter lumen and the interior of the balloon. The invention also includes a flexible guidewire extending axially through the lumen beyond the open end, the guidewire being axially movable within the lumen and having a valve plug disposed near the distal end of the guidewire. The valve plug is of such a size and configuration that is able to close the lumen to fluid flow upon engagement with either the proximal or distal surface of the valve seat. The guidewire and its valve seat are produced in such a fashion that the guidewire may be introduced into the catheter lumen from the distal end thereby allowing the valve plug to contact the distal valve seat or the guidewire may be installed from the proximal end thereby allowing the valve plug to contact the proximal valve surface. Optional, but very desirable, is a catheter body section proximal of the balloon section which is sufficiently stiff to permit use of the guidewire-valve plug in sealing the valve. Preferably, the catheter body section is a multilayered, polymeric tubing that does not kink, "accordion", or stretch upon application of axial force on the guidewire. The most preferred combination of materials is a slippery material as the inner surface of the section surrounded by a high performance engineering polymer such as polyimide.

The catheter may be of a very small diameter or low profile and consequently is quite flexible in its operation.

The balloon inner member may be any of a number of devices allowing fluid communication between the catheter lumen and the interior of the balloon. For instance, the balloon inner member may be a coil, a braid, a braid or coil supported by a tube having holes through its wall, or a tube having holes through its wall.

DESCRIPTION OF THE INVENTION

Figure 1A:
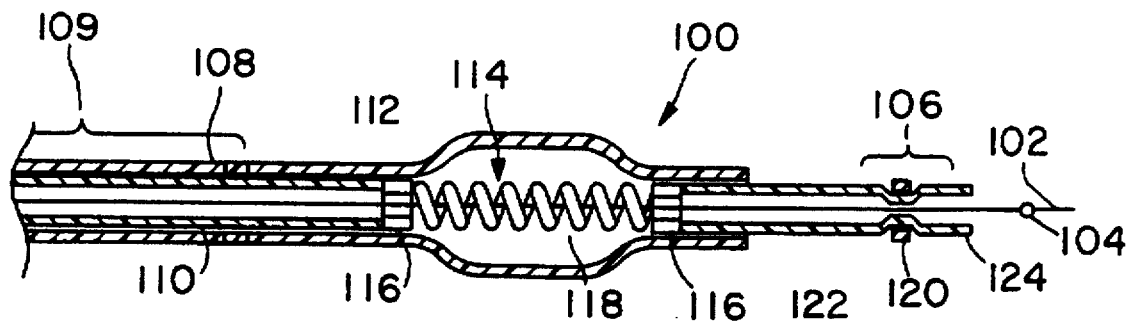
FIGS. 1A and 1B are partial, enlarged, semi-cross sectional depictions of the distal portion of the catheter made according to this invention.
Figure 1B:
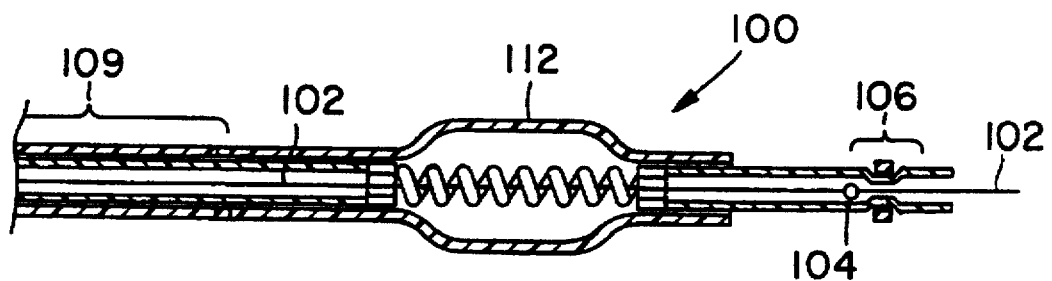

FIGS. 1A and 1B show the distal portion, generally designated (100), of a catheter assembly made according to one embodiment of the invention. FIG. 1A depicts the distal end of the catheter assembly when the guidewire has been inserted with the valve plug (104) distally of the valve section (106). FIG. 1B shows the same catheter assembly (100) with the guidewire (102) with a valve plug (104) positioned proximally of the valve region (106).

Referring to FIG. 1A, the catheter body generally is made up of an outer, thinwall tubing (108) and an inner tubing (110). The balloon body having the balloon inner member (114), which balloon inner member 114 is made up of balloon inner member end sections (116) and a fluid permeable member Distally of balloon (112) is located the valving for the catheter. The valving is a valve section (106) which may be made up of a simple tube having a metal band (120) located so as to form a valve surface (122) proximally of the metal band (120) on the interior of the lumen and a valve surface (124) distally of the band (120).

The catheter (100) has a body section (109) proximal of the balloon section which desirably is made up of an outer tubing (108) which is strong and flexible and an inner tubing member (110). Although there are a number of materials which are suitable for service as the outer tubing, e.g., high density polyethylene (HDPE), low density polyethylene (LDPE), certain highly cross linked silicones, polyesters (including Nylon), polyvinyl chloride, high molecular weight polyurethanes, and various polyimides. Of those materials, a polyimide is the most desirable in that it has a substantial axial strength and is therefore quite "pushable" but also maintains the catheter lumen open even under the severest of pressure. The distal portion of this catheter body is preferably of a much more flexible material such as low density polyethylene.

The inner tubing member (110) is not a required portion of the inventive device but is desirable. The member (110) may be coextruded with the outer tubing (108) or may be a discrete member. Suitably lubricious materials include polysulfides and polyfluoroethylenes. Suitable polyfluoroethylenes include polytetrafluoroethylene, fluoroethylene copolymers having perfluoroalkoxy groups, copolymers of tetrafluoroethylene, hexafluoropropylene, and copolymers of ethylene and tetrafluoroethylene. Most preferred are copolymers of tetrafluoroethylene and hexafluoroethylene.

Although the balloon (112) may be made out of a variety of materials, I have found that the balloon is readily formed from a length of radiation-hardened polyolefin tubing. The chosen polyolefin may be low density polyethylene, high density polyethylene, polypropylene, polybutene, or interpolymers or mixtures of these polymers. In any event, a balloon may be formed by closing one end and applying about 20 to 45 pounds per square inch of pressure within the tube and heating the portion which is to form the balloon to a temperature of between 300°–350° F. Obviously, the length of the balloon formed is determined by the length of the tubing heated. After the balloon is produced in an appropriate size, the heat is removed, and the balloon is allowed to cool. The ends may be cut so to fit in the catheter assembly. Typically the balloon is squeezed to a size near that of the catheter lumen. The ratio of the collapsed diameter of the balloon to the diameter of the catheter just proximal of the balloon is no more than about 1.2 to 1 and preferably no more than about 1.1 to 1. The production of the balloon in this fashion results in a device in which the diameter of the balloon before inflation as compared to the diameter of the balloon after inflation may be about 1:6 or less. The balloon made in this fashion is also axially very certain in size. Unlike elastomeric balloons which may vary in length when inflated, this balloon is essentially isoaxial, particularly when the balloon inner members described herein are utilized. The balloon inner member assembly (114) shown in FIGS. 1A and 1B has two ends (116) and a coil spring (118). This construction will be described in more detail below.

Finally, the valve portion of the catheter assembly is preferably inserted into the portion of the balloon having relatively constant inner diameter. It is held in place by heat welding or gluing or other suitable process. The valve region (106) with its ring (120) and proximal valve surface (122) and distal valve surface (124) may be made by the following procedure. Other procedures are certainly acceptable but I have found that the following procedure produces an excellent result. A polymeric tube having an inside diameter larger than the guidewire is stretched over a mandrel such as a suitably sized stainless steel wire. The ends are locked over the mandrel by heating. A temperature of about 600° F. to appropriate when the chosen polymer is a polyimide. A ring having an appropriate inside diameter is slipped over the tubing. The locked ends of the tubing are cut off to allow the tubing to recover its original dimensions. Polyimide tubing recovers fully by heating it to about 550° F., The ring may be of gold, platinum, platinum-tungsten alloy, stainless steel, or other suitable and, preferably, radioopaque materials. The tubing, upon return to its former diameter, forms distal and proximal surfaces adjacent the ring which serve as valve surfaces for the plug residing on the guidewire.

This distal structure substantially eliminates the possibility of "accordioning" when the distal valve surface (124) is used as the valve seat.

FIG. 1B simply shows the insertion of the guidewire (102) from the proximal end of the catheter so to allow the valve plug (104) to seat against the proximal valve surface (122). In this instance the valve is seated by pushing the guidewire (102) distally prior to filling the balloon (112) with a fluid via the catheter lumen.

Some clinical situations require that the balloon catheter be used in conjunction with a specific or preferred guidewire to gain access to the vascular anatomy. Some clinical situations also require that site-specific drugs such as urokinase for clot dissolution or contrast materials for fluoroscopic imaging be delivered through the catheter before a balloon angioplasty is performed. During such clinical situations, the inventive catheter may be used in conjunction with any guidewire of compatible size to gain access to the vascular anatomy. The catheter may be used as an infusion catheter if so desired. If a balloon angioplasty is then desired, the guidewire are removed and the inventive guidewire (102) having the valve plug is introduced at the proximal end of the catheter, engaged with the valve surface (122) in valve region (106), and the balloon inflated. This procedure of not replacing the infusion catheter by a balloon catheter and of merely substituting guidewires is quite efficient and is desirable in procedures such as cerebral angioplasty where time is a critical element.

Figure 2:
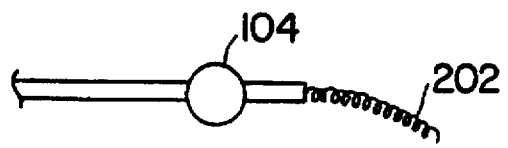
FIG. 2 shows a close up side view of the distal portion of a guidewire suitable for use in this invention.

The guidewires useful as guidewire (102) in these devices are straightforward. The shape of the valve plug (104) is relatively unimportant so long as it meshes adequately with the valve surfaces formed in valve region (106). I have found that a spherical surface is adequate and desirable. Moreover, in addition to the relatively simple guidewires of varying thicknesses as are known in this technology and shown in FIGS. 1A and 1B, the guidewire used in this invention may additionally have a flexible tip (202) as in shown in FIG. 2. These flexible tips are well known. They are used with the aid of fluoroscopy to advance the catheter through the vasculature. The body of the catheter (with the collapsed balloon) is moved distally along the guidewire to a site where the guidewire may be again introduced farther into the vasculature until a desired site is attained. Obviously, use of the guidewire in this fashion typically requires that the guidewire be introduced into the catheter body from the distal end rather than from the proximal end.

FIGS. 3A through 3D show a variety of balloon inner members which help to provide axial length stability to the balloon (112) shown in FIGS. 1A and 1B and maintain the lumen within the valve region in general colinear relationship with the lumen of the more proximal portions of the catheter assembly.

Figure 3A:
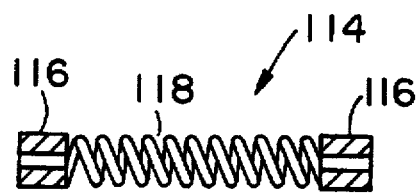
FIGS. 3A and 3B show side views of two variations of the balloon inner member.

FIG. 3A shows a simple balloon inner member (114) as was included in the devices shown in FIGS. 1A and 1B. Balloon inner member (114) is made up of two ends (116) and a spring (118). The ends serve to allow mounting of the balloon inner member (114) in the sections of the catheter having reasonably constant diameter. The inner diameter may be large enough to pass the valve plug (104) therethrough or may be smaller to allow only the guidewire to pass. The ends have, of course, a lumen allowing a guidewire to pass completely through the ends and through the intermediate coil (118). The ends (116) may be attached to the coil (118) by any suitable means including gluing, shrink wrapping, heat welding, solvent welding, and a host of other ways. The coil (118) involved is one having an inside diameter at least larger than that of the guidewire passing through it. Typically the inside diameter of coil (118) would be 0.020 to 0.035 of an inch. The diameter of coil wire typically would be in the region of 0.003 to 0.005 of an inch. The coil itself (118) may be wound in such a way that there is little space between windings. Ideally, the windings are flush with each other. That is to say the pitch of the coil is equal to the diameter of the wire making up the coil. The coil may be of any suitable material although gold alloys, silver alloys, platinum alloys, and other biocompatible materials having significant springiness are appropriate in this service. Polymeric materials or carbon fiber materials having the appropriate physical characteristics are also quite workable.

Figure 3B:
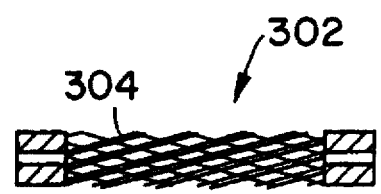

FIG. 3B shows braided balloon inner member in which a braid (304) is substituted for the spring or coil (118) shown in FIG. 3A. The materials of construction and size of the wire or ribbon making up the braid are quite similar to the coil (118) shown in 3A.

Figure 3C:
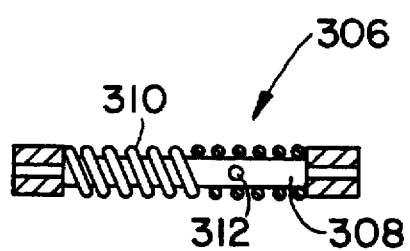
FIGS. 3C and 3D show enlarged partial cross-sections of still further variations of the balloon inner member.

FIG. 3C shows a device similar to that shown in FIG. 3A, in that a coil is used to permit the flow of fluid from the lumen inside the balloon inner member (306) into the body of the balloon, as is shown in FIG. 1A or 1B. In this instance, the balloon inner member (306) additionally contains an interior tubing (308) coaxial to the coil (310). The inner tubing (308) has a number of orifices (312) to permit fluid flow. The inner tubing (308) may be of metal, polymer, carbon or other suitable biocompatible material. Desirably the tubing is a polymeric material such as a polyimide, which is stiff, strong, and biocompatible. The ends of the inner tubing (308) adhere to the respective ends. FIG. 3C is a partial cutaway showing both the interior and the exterior of the balloon inner member (306).

Figure 3D:
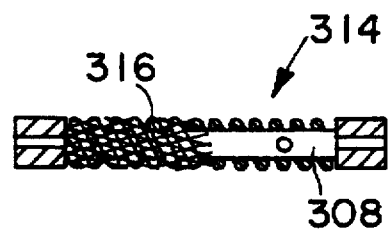

FIG. 3D shows a partial cutaway of a balloon inner member (314) which is analogous to that shown in FIG. 3C, except that instead of coil (310), the exterior of the inner tubing (308) is a braided material (316). The coil of FIG. 3C and the braid of FIG. 3D are optional.

The catheter assembly of the invention is operated in similar fashion to other valve balloon catheters. In such operation, the guidewire is advanced into the vasculature to a desired site, and the catheter body is tracked over the guidewire. The location of the guidewire and the balloon within the vessel may be determined by conventional radiology techniques. Once the balloon is at the desired site within the vessel, the catheter lumen is flushed by injecting fluid through the catheter lumen, the valve plug (104) is seated against the distal valve surface (124) or the proximal valve surface (122), depending upon the end from which the guidewire was introduced, by axially manipulating the guidewire. The valve plug (104) blocks the distal opening of the catheter tube. The balloon is then inflated by injecting fluid through the catheter lumen. If desired, controlled distal leakage of the fluid from the catheter tip may be achieved by a slight adjustment in the tightness of the seating between valve plug (104) and the respective valve seating areas. The balloon may be deflated by withdrawing fluid from the catheter lumen.

Many alterations and modifications may be made by those of ordinary skill in the art without departing from the spirit and scope of this invention. The illustrated embodiments have been shown only for purposes of clarity. The examples should not be taken as limiting the invention as defined by the following claims, which claims include all equivalents, whether those equivalents are now or later devised.

I claim as my invention:

1. A balloon catheter assembly comprising
   a proximal shaft with a proximal coupler; and
   a distal balloon region that has an expandable balloon extending distally of the proximal shaft and a catheter tip extending distally of the expandable balloon, and that also forms a lumen that is in fluid communication with the proximal coupler, said catheter tip having a circumferentially cinched portion of reduced inner and outer diameter which forms a valve seat within said lumen;
   wherein said valve seat is adapted to engage a valve plug formed on a control wire that is coaxially disposed within said lumen and thereby form a fluid seal.

2. The balloon catheter assembly of claim 1, further comprising a control wire having proximal and distal ends and a valve plug that is disposed near its distal end, and that is adapted to engage said valve seat by sliding axially through the catheter lumen, thereby forming a fluid seal.

3. The balloon catheter assembly of claim 2, wherein said valve seat further comprises proximal and distal valve surfaces, and said control wire is adapted to engage the valve seat on either of the valve surfaces with the valve plug to thereby form a fluid seal.

4. The balloon catheter assembly of claim 3, wherein said control wire is a guidewire having a proximal end portion and a shapable distal tip.

5. The balloon catheter assembly of claim 2, wherein the inflatable balloon additionally comprises proximal and distal ends and a balloon inner member extending therebetween, said balloon inner member allowing fluid communication between the lumen and the inflatable balloon and being adapted to allow axial passage of the control wire.

6. The balloon catheter assembly of claim 1, wherein the circumferentially cinched portion of the catheter tip further comprises a circumferential radiopaque band.

7. A balloon catheter comprising a proximal shaft with a proximal coupler; and a distal balloon region having an expandable balloon extending distally from the proximal shaft, a catheter tip extending distally from the expandable balloon, a lumen formed coaxially within the expandable balloon and catheter tip and in fluid communication with the proximal coupler, and a valve seat in the catheter tip having a bore of reduced inner diameter within the lumen and which allows for coaxial passage of a control wire, said valve seat also forming proximal and distal valve surfaces each adapted to engage a valve plug formed on the control wire and thereby seal said lumen for fluid pressurization.

8. The balloon catheter assembly of claim 7, further comprising a control wire having proximal and distal ends and a valve plug that is disposed near its distal end and that is adapted to engage either the distal or proximal valve surfaces by sliding axially through the catheter lumen, thereby forming a fluid seal for fluid pressurization.

9. The balloon catheter assembly of claim 8, wherein said control wire is a guidewire having a proximal end portion and a shapable distal tip.

10. The balloon catheter assembly of claim 8, wherein the inflatable balloon additionally comprises proximal and distal ends and a balloon inner member extending therebetween, said balloon inner member allowing fluid communication between the lumen and the inflatable balloon and being adapted to allow axial passage of the control wire.

11. The balloon catheter assembly of claim 8, wherein a portion of said catheter tip is circumferentially cinched to form said valve seat.

\* \* \* \* \*

UNITED STATES PATENT AND TRADEMARK OFFICE

CERTIFICATE OF CORRECTION

PATENT NO. : 5,683,410

DATED : November 4, 1997

INVENTOR(S) : Gene Samson

It is certified that error appears in the above-identified patent and that said Letters Patent is hereby corrected as shown below:

Column 1, line 35, delete "is", and insert -- its --.

Column 1, line 63, delete "is", and insert -- its --.

Column 2, line 20, delete "that", and insert -- than --.

Column 2, line 50, after "that", insert -- it --.

Column 3, line 34, after "body", insert -- (112), --.

Column 3, line 37, after "member", insert -- (118). --.

Column 5, line 41, delete "spring", and insert -- coil --.

Signed and Sealed this

Twenty-eighth Day of July, 1998

Attest:

BRUCE LEHMAN

Attesting Officer

Commissioner of Patents and Trademarks